United States Patent [19]

Ikonen

[11] Patent Number: 4,792,432
[45] Date of Patent: Dec. 20, 1988

[54] METHOD FOR PERFORMING A LIQUID ANALYSIS AND AN ANALYTICAL ELEMENT FOR USE IN THE METHOD

[75] Inventor: Veijo Ikonen, Halujärventie, Finland

[73] Assignee: Orion-yhtyma Oy, Espoo, Finland

[21] Appl. No.: 10,385

[22] Filed: Feb. 3, 1987

[30] Foreign Application Priority Data

Feb. 4, 1986 [FI] Finland ................................. 860509

[51] Int. Cl.[4] ........................ G01N 9/30; G01N 33/06
[52] U.S. Cl. ...................................... 422/72; 422/74;
422/101; 436/23; 436/70; 436/165
[58] Field of Search ...................... 422/58, 60, 57, 59,
422/69, 72, 74, 101; 436/22, 23, 24, 70, 45, 165,
169, 170, 177; 494/16

[56] References Cited

U.S. PATENT DOCUMENTS

| | | | |
|---|---|---|---|
| 658,250 | 9/1900 | Erfmann | 422/101 |
| 3,996,001 | 12/1976 | Sanz et al. | 436/165 |
| 4,270,921 | 6/1981 | Graas | 422/72 |
| 4,557,600 | 12/1985 | Klose et al. | 436/45 |
| 4,588,555 | 5/1986 | Provonchee | 436/45 |

Primary Examiner—Benoit Castel
Assistant Examiner—Jill Johnston
Attorney, Agent, or Firm—Burgess, Ryan & Wayne

[57] ABSTRACT

The present invention relates to a method for making liquid analysis and to an analytical element to be used in the method. The method is especially suitable for analysing organic fluids, like blood. The analytical element is of the integrated element type and consists of two parts of certain volume, which parts are connected to each other so that they form a pair of communicating vessels. In the preferred embodiment the element consists of two arms, one is a descending arm and the other is an ascending arm. There is a liquid carrier phase in the end of the descending arm and said phase is dipped into the liquid to be analysed for dosing the liquid in a quantitative manner. An external gravitational field like a centrifugal force is used to move the liquid inside the element through a diffusion zone and a reaction zone to a detection zone for the measurement of the result. In the method like in the element the law of communicating vessels is at least a contributory factor for limiting the flow of the liquid to be analysed, since the surface of the liquid in both vessels will be on the same niveau.

18 Claims, 3 Drawing Sheets

METHOD FOR PERFORMING A LIQUID ANALYSIS AND AN ANALYTICAL ELEMENT FOR USE IN THE METHOD

FIELD OF THE INVENTION

The present invention relates to a method for performing a liquid analysis and to an analytical element for use in the method. The liquids to be analysed include in particular organic fluids, such as whole blood, plasma or serum, or, for example, urine. However, there is nothing to prevent the analysis of, for example, water or colloidal solutions. The analytical element is specifically of so-called integrated type, which here means that all of the steps necessary for the analysis take place in one and the same element.

In blood analyses the aim has been an integrated analytical element, but it has not been possible to develop an element by means of which the result could be obtained by only taking the sample and determining the result. Since reproducibility is, of course, one requirement, the developing has been especially difficult and has not been successful.

One of the factors most hampering accuracy in blood analyses is hematocrit, the wide variation of which causes considerable errors in the results of analysis. The principal disadvantage due to hematocrit has been the variation of blood viscosity, depending on the hematocrit value. Clinical results are therefore usually reported as results of plasma or serum, in which case hematocrit has been eliminated by separating the blood cells from the sample even before the analysis. If, on the other hand, whole blood is used, allowance must be made for the fact that the results are not reproducible.

BACKGROUND OF THE INVENTION

In so-called integrated analytical elements the aim is that all of the handling of the sample is carried out inside the element. Thus the aim is that the pre-treatment of the sample, its quantitative dosing and the quantitative dosing of reagents can be carried out inside the element and not as separate steps outside the element. When speaking of quantitative analysis, there are certain known devices in which the aim has been an integrated analytical element. Such devices have been disclosed, for example, in GB Pat. No. 1 440 464, U.S. Pat. Nos. 3,992,158, 4,066,403 and 4,363,874, as well as in CA Pat. No. 1,162,075, DE Application No. 31 33 538 and GB Application No. 2,095,404.

All of the above-mentioned publications describe devices in which the zones required for the analysis are placed in layers one above the other. The analyte is dosed into one layer, and in the second layer there occur the suitable reactions on the basis of which the desired response is then determined in one way or another. The publications also describe various improvements in the materials of the zones, the dosing systems, etc.

As mentioned above, hematocrit of whole blood constitutes the biggest hindrance to accuracy. If it is desired to use only plasma or serum of the blood, hematocrit has been eliminated, but the separation requires a separate step and separate apparatus for the separation procedure. In addition to increased work and generally increased difficulty in obtaining the results of the determination, one consequence is that a person trained for the work is required for the work steps.

Another hindrance to accuracy is that the materials used do not necessarily lead to uniform diffusion from one layer to another. Also, the difference in the viscosity of the sample, which is due to, for example, variation of hematocrit, causes problems in reproducibility.

OBJECT OF THE INVENTION

The object of the present invention is to avoid the above-described disadvantages typical of known analytical elements. The object is to produce an integrated analytical element which does not require pre-treatment of the sample outside the element, except for the taking of the sample. By using the method and analytical element according to the invention it is, furthermore, possible to perform the analysis in an always equally reproducible manner even on whole blood in which blood cells are present. A further object of the invention is to provide a method and a device by means of which an analysis can be performed by a person who has not been given special training in laboratory work, since the factors which cause errors have according to the invention been minimized.

SUMMARY OF THE INVENTION

The invention is based on the surprising observation that in practice all of the factors hampering accuracy can be avoided by the use of an artificial (external) gravitational field, especially centrifugal force, in an analytical element designed for the purpose, and an always equally good, reproducible final result can be obtained even when whole blood is used. Another basic idea of the invention is that, according to the invention, in the separation of the cells and in the primary dosing of the sample the law of communicating vessels is used as the principal or a contributing factor to limit the flow of the liquid to be analysed. Primary dosing here means the quantitative dosing of the sample into that part of the element in which the determining of the response and the reactions preceding the determining or proceeding during the measuring occur.

BRIEF DESCRIPTION OF THE DRAWINGS

The invention is described below in greater detail with reference to the accompanying patent drawings, in which.

DESCRIPTION OF THE PREFERRED EMBODIMENT

Figure 1:
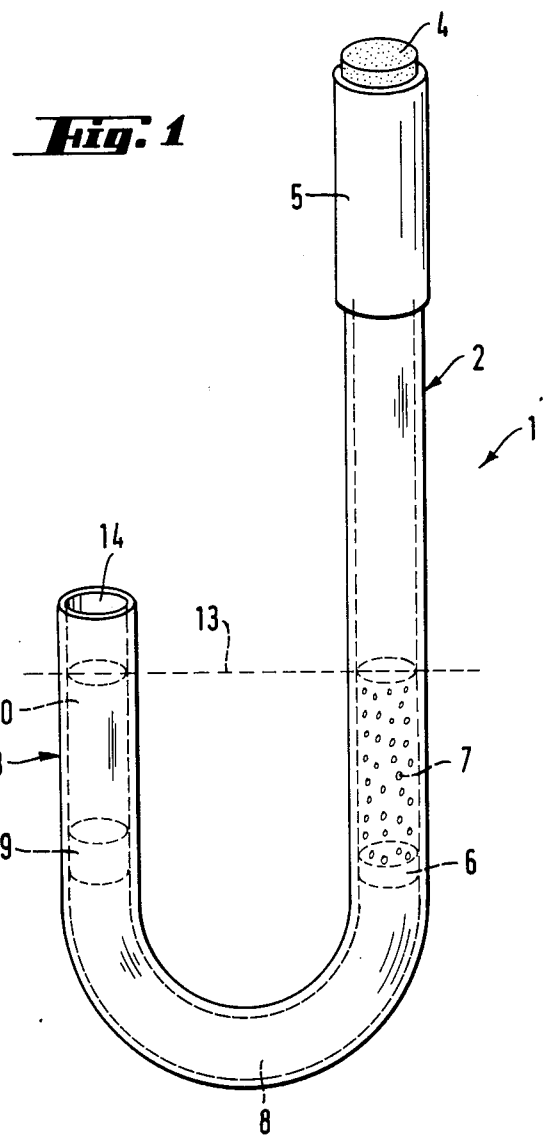
FIG. 1 depicts the general principle of the device according to the the invention.

FIG. 1 depicts the basic principle of that embodiment of the device according to the invention which has been considered to be best. The device 1 is made up of a U-shaped tube which has been made specifically of glass, although a plastic tube is also suitable for the purpose. One arm of the tube is here called the descending arm 2 and the other (the shorter one in the figure) is called the ascending arm 3. At the end of the descending arm is the liquid carrier phase 4, which is dipped into the sample to be analysed in order to absorb a certain sample volume into the carrier phase. The phase 4 is in a plastic sleeve 5, or a similar device, and can thus be easily pushed to the end of the descending arm 2. After the absorbing of the sample the entire analytical device 1 is preferably placed in a centrifuge, the speed of rotation of which is set at a suitable value. The centrifugal force causes the sample to start moving from the carrier phase 4 and to pass to the filter 6, where the blood cells 7 separate from the blood sample.

The blood cells do not pass through the filter 6, and the serum continues its movement towards the ascending arm 3, and comes at the same time into contact first with the diffusion zone 8 and thereafter with the reaction zone 9, whereafter it arrives, in accordance with the law of communicating vessels, in the detection zone 10, in which the reaction change caused by the reaction zone 9 is determined in the manner suitable in each given case. The place of the filter 6 is selected in a manner appropriate in each given case.

The place of the filter is chosen in a way which is suitable for the purpose. A place of the filter 6 which suits better for the purpose is, instead of the place in the descending arm 2, the place in the ascending arm 3. The reason for this is that the filter 6 is quite easy to get clogged and when the filter is located in the ascending arm 3 the pressure of the fluid acting against the filter is quite much smaller than in the descending arm.

As already mentioned above, the invention is based on the realization that an external gravitational field is used, by means of which the flow of the liquid constituting the sample is caused to settle at certain values, always and every time the same manner. When a U-tube is used as the analytical device, the liquid level in the descending 2 and the ascending arm 3 is made to settle always at the same height, which is illustrated by the dotted line 13 in the figures. If the position of the zones used is selected suitably, the response can always be determined in a reproducible manner at the end of the ascending arm 3. If, however, it is so desired, the height of the liquid surfaces can be selected so that the moving of the last stage of the analyte to its final position takes place by diffusion.

Figure 3:
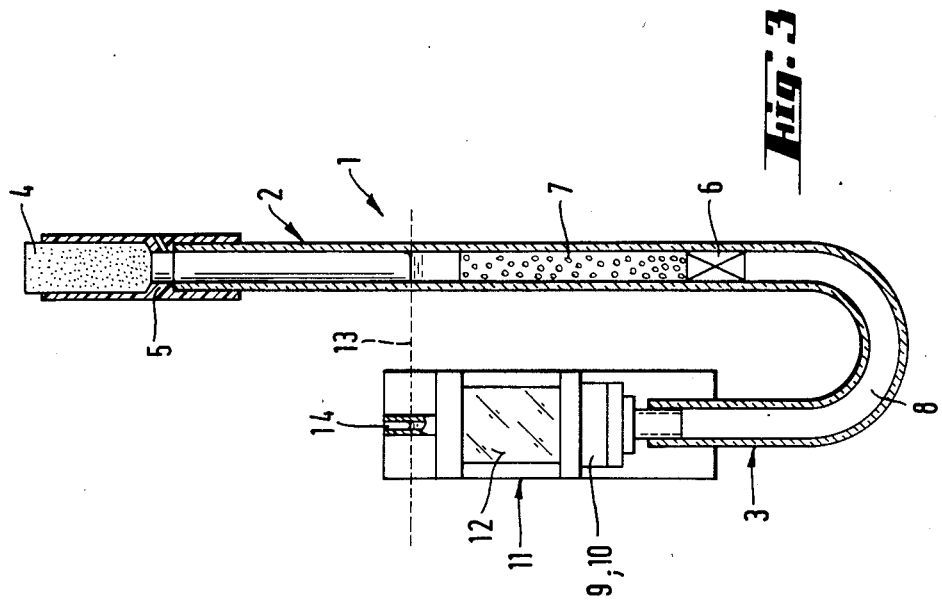
FIG. 3 depicts the same device, applied to photometric determination.
Figure 2:
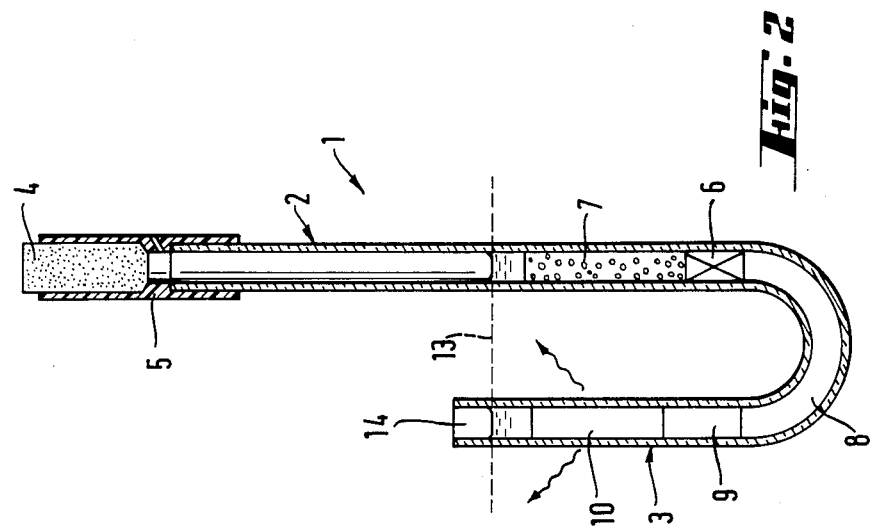
FIG. 2 depicts a device according to the invention, applied to luminometric determination.

FIGS. 2 and 3 depict luminometer and photometer embodiments of the analytical element according to the invention for the determination of the response. The reference numerals indicate the same as in FIG. 1. In the embodiment of FIG. 3 a disposable cuvette 11 is used at the end of the ascending arm 3 of the element; by means of this cuvette it is possible to carry out the desired photometric determination directly without any extra preparations for the determination. The cuvette 11 has a window 12 which is made up of two glass sheets or sheets of similar material, with capillary forces effective between them. Thus the liquid to be analysed will diffuse to the measuring window 12 under the effect of the capillary forces. The diffusion zone 8 extends all the way to the lower part of the cuvette and the reaction zone 9 and the detection zone 10 combined in this embodiment.

Figure 4:
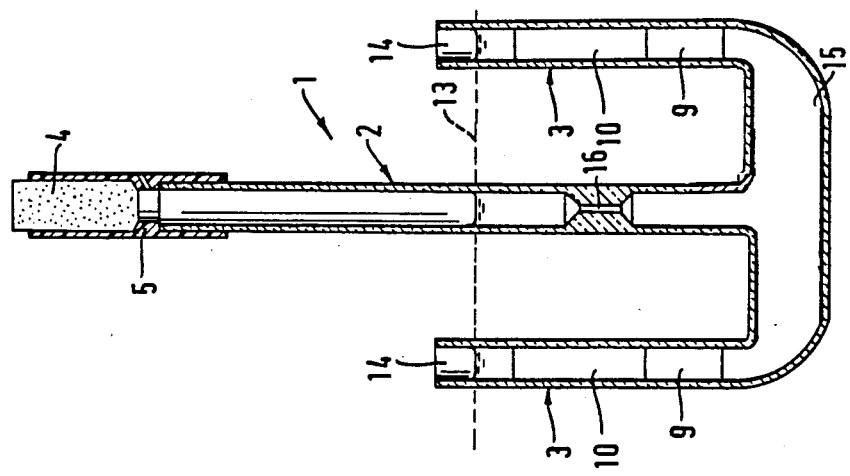

In certain cases it is possible to leave the filter completely away. This kind of alternative is described in FIG. 4 which contains two amendments compared with the alternatives shown before. If the filter is left away it is wise to restrict the fluid flow so that the external gravitation field can stop the cells or the solid particles of the specimen on the bottom 15 of the tube 1. For the given purpose it is possible to use a capillary portion 16 in the descending arm 2. The bottom 15 of the tube may be widened, like shown in FIG. 4, so that there still is an area without any cells in the uppermost part of the bottom 15 after the gravitational field has separated the solid particles/cells on the bottom. In this way it has been made sure that the cells do not move to an undesired place with the forced flow.

Figure 5:
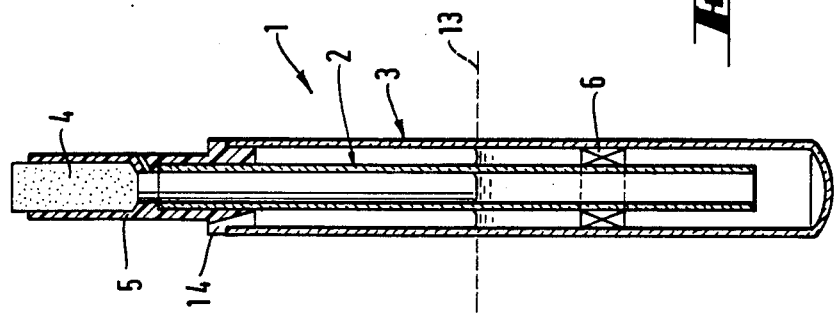
FIG. 4 depicts another alternative of the device according to the invention and FIG. 5 depicts still another alternative according to the invention.

FIG. 5 shows a further alternative way to use the idea according to the invention. The descending arm 2 is in this embodiment a tube which is at least partly open in the lower end. The ascending arm is a concentrically located tube 3 with a larger diameter around arm 2. The lower end of tube 3 is closed. The invention according to this embodiment works in exactly the same way as the embodiments which have been described before. The flow of the fluid is easy to be restricted by for instance making a small bore in the bottom of tube 2. Filter 6 is not needed in such circumstances even though it is still possible to use the bore and the filter.

Thus the same basic principle and a structurally similar analytical element is used in all of the embodiments.

The liquid carrier phase 4 of the analytical element is typically strongly hydrophilic, in which case the dosing of the sample, specifically of blood, takes place rapidly with the aid of capillary forces, so that the brief dipping of the liquid carrier phase into the sample is a sufficient step for carrying out a semi-quantitative or quantitative preliminary dosing. Cellulose, cotton, felt, filter paper, gelatin, agarose and various polymeric materials are examples of excellent materials for the liquid carrier phase. The free volume of the liquid carrier phase is preferably 15-95%. The phase may be part of the frame structure of the analytical element or a separate part, as explained above. The phase may be by structure a fibrous or a porous material or an individual capillary tube or a capillary system.

The filter 6 separates the blood cells out from the serum so that the cells will no longer be able to interfere with the determinations to be carried out later. The pore size of the filter is, of course, smaller than the size of blood cells, so that the cells should not pass through the filter. Typically blood cells are 7-30 $\mu$m in size, so a suitable pore size for the filter is, for example, 0.1-5 $\mu$m. The separation of the cells can also be achieved by using adsorption, in which case the filter may be made up of the same material as the layer 8. It is evident that, if the material to be analysed is something else than whole blood, the pore size of the filter 6 must be such that it is capable of filtering the desired particles out from the liquid.

By selection of the material of the diffusion zone 8 it is possible to influence different quantities affecting the analysis. The material of the diffusion zone in particular is a crystalline material having a very small crystal size. Examples of suitable materials include diatomite and polymeric structures, in which case the particle size is, for example 80-120 $\mu$m. The above-mentioned materials can be used dispersed in, for example cellulose esters, polyvinyl alcohol or gelatin. By adjusting the available volume of the diffusion zone it is possible to use this phase for selective filtration, for removal of interference, for various chromatographic applications, for competitive immunologic reactions, etc.

The reaction zone 9 may comprise one or several zones in which the reactions necessary for detection occur. The zones contain the reagents necessary for the reactions.

The detection zone 10 may be the same zone as the reaction zone 9, but it can also be a separate zone. The principle is that the response which the purpose is to determine in the detection zone is determinable in the zone. The principle of determination can, of course, vary, and an indication reaction suitable for the method in question is used in each case. Photometry and luminometry were mentioned above as measuring principles, but the principle and analytical element according to the invention can also be applied at least to reflectometric and fluorometric determinations.

The principle according to the invention can also be applied to carrying out several different determinations simultaneously. In such a case a device so modified is used that the ascending arm 3 is divided into several separate, parallel arms, each of them containing the reagents specifically for this reaction. In such a case, of course, a different color or other reaction is obtained in each arm, the property detected by them can be determined independently of the others. In certain special applications the device may also have several descending arms.

As shown in the above description, by the method and analytical element according to the invention considerable advantages are gained over known devices and conventional analytical techniques. The entire analytical procedure is very simple to carry out, and thus it does not require personnel with laboratory training. The method and device according to the invention crucially facilitate the availability of analysis services.

By using the analytical element according to the invention it is possible to manage without any pre-treatment of the sample and still achieve a quantitative dosing of the sample. Since all reagents have, as early as the preparation stage of the element, been suitably absorbed at predetermined points in the element, the dosing of the reagents is also quantitative. Likewise, it is possible to accomplish the desired number of reactions with the analyte, in which case the determination can always be carried out reproducibly.

The accuracy of the determination is affected specifically by the forced flow achieved in accordance with the invention. Since the flow is produced by means of hydrostatic pressure, the temperature does not in practice affect the dosing of the sample at all. Diffusion can also be controlled better in accordance with the invention than in known devices, since the forced liquid flow reduces the back-flow caused by diffusion. On the other hand, according to the invention it is also possible to let diffusion have its own role, as was already mentioned above. It will also be partly the role of diffusion to distribute the liquid in the lateral direction evenly over the entire area of the analytical element. If necessary, diffusion can also be used for special applications to ensure the desired flow inside the device.

The principle, used according to the invention, of the utilization of the law of communicating vessels in the analysis procedure means that the liquid flows always settle at the same point in the device, in which case accuracy is ensured even in that respect. By using a force of the desired magnitude for moving the liquid, for example a certain speed of rotation in the centrifuge, the moving speed of the liquid can be controlled so that the determination can be reproduced with precision. In the ascending arm the accuracy of the primary dosing can, when necessary, be ensured by taking advantage of the surface tension of the sample, by arranging that the gas-flow opening 14 is of a suitable size or in some other conventional way.

For an expert in the art it is fully evident that the invention is not limited with respect to its determination principle or desing, etc., only to what has been pointed out above by way of example, but for an expert in the art the polishing of the details is only conventional work.

The method and analytical element according to the invention can be easily applied also to an automatic analysis system.

I claim:

1. An analytical device for analyzing colloidal liquid substances whereby a liquid sample is moved within said device consisting essentially of in combination:
   (a) a descending hollow, tubular-shaped arm communicating at its lower portion with at least one ascending hollow, tubular-shaped arm, said arms forming a continuous U-shaped tubular system of substantially uniform diameter;
   (b) sample introduction means at the top end of said descending arm for the introduction of a liquid sample;
   (c) filter means located within said arms through which said liquid sample passes;
   (d) means providing a reaction zone within said ascending arm wherein said liquid sample undergoes reaction; and
   (e) means providing a detection zone within said ascending arm for detecting a reaction.

2. The device of claim 1 wherein said detection zone is a disposable a cuvette for photometric determination.

3. The device of claim 1 wherein said filter means is of sufficient porosity to separate cells from whole blood.

4. The device of claim 3 wherein said filter means has a porosity of from 0.1 to 5 $\mu$m.

5. The device of claim 1 wherein a diffusion zone is disposed between said filter means and said reaction zone.

6. The device of claim 5 wherein said diffusion zone is combined with said reaction zone.

7. The device of claim 1 containing a plurality of ascending arms and wherein each of said plurality of ascending arms communicates with said descending arm at its lower end, forming a continuous U-shaped zone of substantially uniform diameter.

8. The device of claim 7 wherein each of said plurality of ascending arms contains reaction and detection zones for different properties of said liquid substance.

9. The device of claim 1 wherein said sample introduction means is detachable from the top end of said descending arm.

10. The device of claim 9 wherein said sample introduction means contains a sleeve for attachment to said descending arm.

11. The device of claim 9 wherein said sample introduction means contains a fibrous or porous material.

12. The device of claim 9 wherein said sample introduction means contains a capillary system.

13. A method for analyzing colloidal liquid substances which comprises the steps of:
   (a) introducing a sample of a liquid substance into the top end of the descending arm of the analytical device of claim 1;
   (b) applying centrifugal force to said device to cause said liquid sample to move;
      (i) from said sample introduction means to said filter means to remove from said liquid sample, undesirable particulate material;

(ii) from said filter means to said reaction zone wherein said liquid sample undergoes a reaction with components in said zone;
(iii) from said reaction zone to said detection zone, and
(c) detecting and measuring the reaction which occurred in said reaction zone.

14. The method of claim 13 wherein the sample of liquid substance to be analyzed is obtained by dipping a sample carrier attached to the top of the descending arm of said device into a liquid sample.

15. The method of claim 13 wherein the liquid sample to be analyzed is whole blood.

16. The method of claim 13 wherein the filter means has a porosity sufficient to retain blood cells.

17. The method of claim 13 wherein said reaction zone and said detection zone are located in the same portions of the ascending arm.

18. The method of claim 13 wherein a diffusion zone is located between said filter zone and said reaction zone.

* * * * *